US011674876B2

(12) United States Patent
Akkutlu et al.

(10) Patent No.: US 11,674,876 B2
(45) Date of Patent: Jun. 13, 2023

(54) METHOD FOR ESTIMATION OF FLUID STORAGE CAPACITY OF ROCK SAMPLES AND OTHER POROUS MATERIALS UNDER EFFECTIVE STRESS

(71) Applicant: The Texas A&M University System, College Station, TX (US)

(72) Inventors: Ibrahim Yucel Akkutlu, College Station, TX (US); Ivan C. Aldana, College Station, TX (US)

(73) Assignee: The Texas A&M University System, College Station, TX (US)

(*) Notice: Subject to any disclaimer, the term of this patent is extended or adjusted under 35 U.S.C. 154(b) by 79 days.

(21) Appl. No.: 17/332,251

(22) Filed: May 27, 2021

(65) Prior Publication Data
US 2021/0372914 A1    Dec. 2, 2021

Related U.S. Application Data

(60) Provisional application No. 63/031,084, filed on May 28, 2020.

(51) Int. Cl.
*G01N 15/08*    (2006.01)
*G01N 33/24*    (2006.01)

(52) U.S. Cl.
CPC ....... *G01N 15/088* (2013.01); *G01N 15/0806* (2013.01); *G01N 15/0826* (2013.01); *G01N 33/24* (2013.01)

(58) Field of Classification Search
CPC .... G01N 15/00; G01N 15/08; G01N 15/0806; G01N 15/0826; G01N 15/088; G01N 33/24
See application file for complete search history.

(56) References Cited

FOREIGN PATENT DOCUMENTS

| CN | 110208164 A | * | 9/2019 | ............. G01N 13/00 |
| CN | 110296921 A | * | 10/2019 | ......... G01N 15/0826 |
| CN | 112730187 A | * | 4/2021 | ............. G01N 15/08 |

OTHER PUBLICATIONS

Aldana Gallego, Ivan C., et al., A Laboratory Method for Estimation of Storage Capacity of Rock Samples Under Effective Stress, SPE Europec featured at 81st EAGE Annual Conference & Exhibition, Jun. 3-6, 2019 [15 pages].

* cited by examiner

*Primary Examiner* — Nguyen Q. Ha
(74) *Attorney, Agent, or Firm* — Winstead PC

(57) ABSTRACT

The system includes a gas tank. A reference volume is fluidly coupled to the gas tank. A coreholder fluidly is coupled to the reference volume. A sample is disposed in the coreholder. A fluid pump is fluidly coupled to the coreholder. A first pressure transducer is fluidly coupled between the fluid pump and the coreholder. The first pressure transducer measures a confining pressure. A second pressure transducer is fluidly coupled to the coreholder. The second pressure transducer measures upstream pressure within the coreholder.

19 Claims, 6 Drawing Sheets

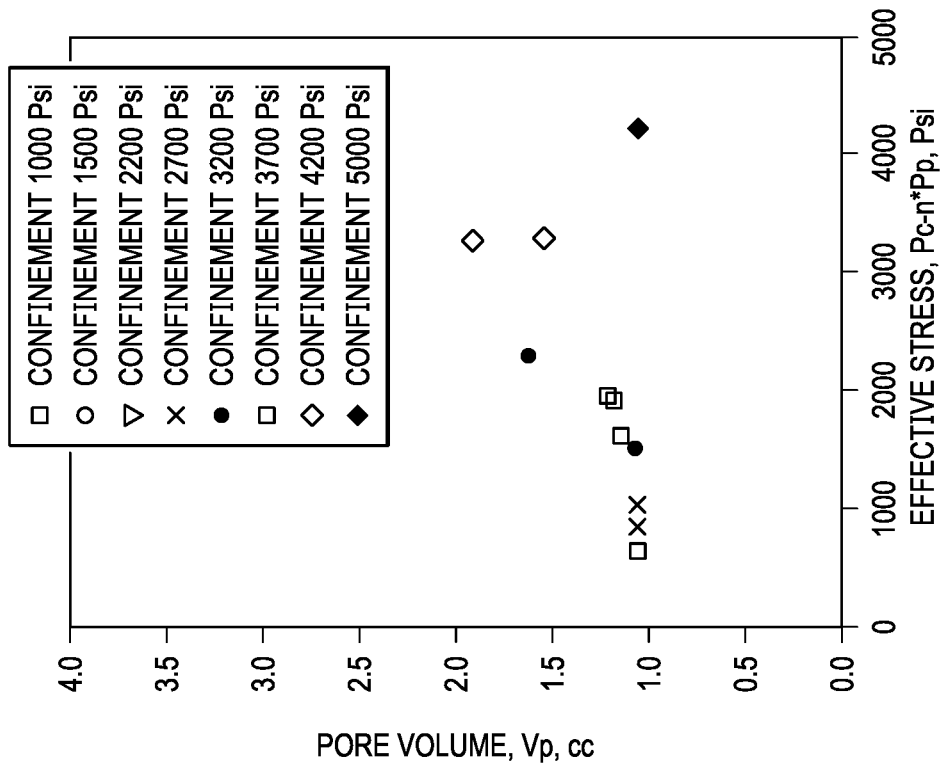
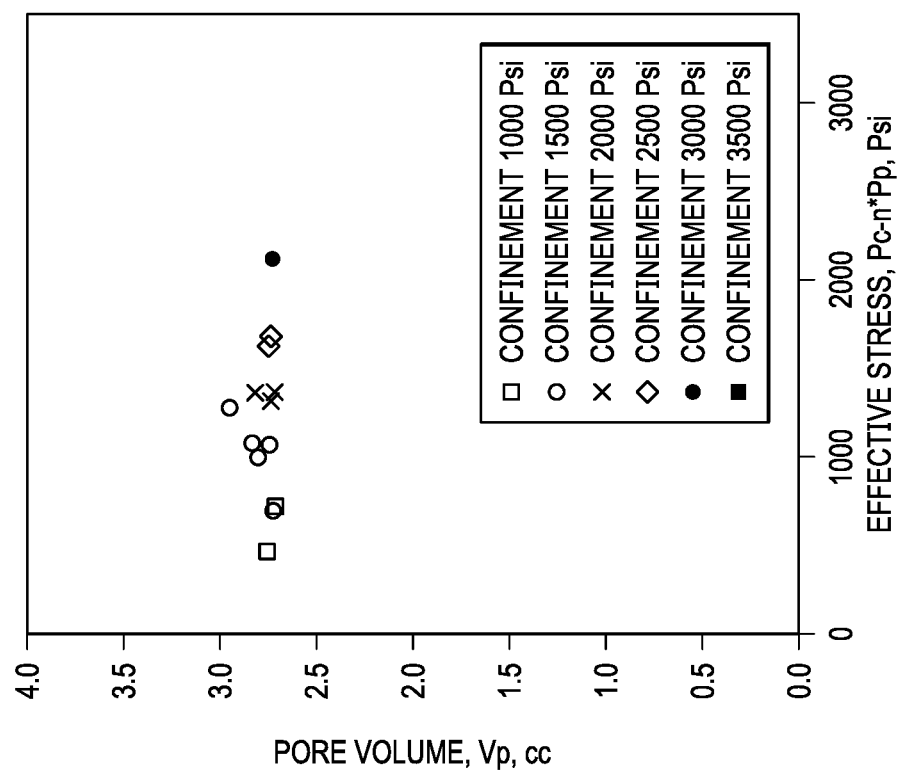
FIG. 3B
FIG. 3A

METHOD FOR ESTIMATION OF FLUID STORAGE CAPACITY OF ROCK SAMPLES AND OTHER POROUS MATERIALS UNDER EFFECTIVE STRESS

CROSS-REFERENCE TO RELATED APPLICATIONS

This application claims priority to, and incorporates by reference, the entire disclosure of U.S. Provisional Patent Application No. 63/031,084, filed on May 28, 2020.

TECHNICAL FIELD

Aspects of the disclosure relate to a method of estimating porosity of rock samples and more particularly, but not by way of limitation, to a method of simulating downhole conditions for estimation of porosity.

BACKGROUND

This section provides background information to facilitate a better understanding of the various aspects of the disclosure. It should be understood that the statements in this section of this document are to be read in this light, and not as admissions of prior art.

Traditionally, fluid-storage capacity of porous materials, such as oil- and gas-bearing rocks, is measured in the laboratory in the absence of stress. The porous sample could be cylindrical (disc-shaped) or crushed particles. Pore volume or porosity (i.e., pore volume/bulk volume) is measured as an indication of the fluid storage capacity of the sample. However, it is widely recognized that the storage capacity could change when the sample is subjected to stress. This change is controlled by the mechanical behavior of the sample under stress. The present disclosure relates generally to systems and methods developed to estimate the fluid storage capacity of a sample under effective stress.

Additionally, mechanical tests are available and can be used to measure the Biot's coefficient. However, these tests are expensive, time consuming, and destructive. Furthermore, the coefficient is estimated indirectly as a function of the applied external load and the measured volumetric strain, no measurement fluid is involved.

Another way of simultaneously measuring the pore volume and the Biot's coefficient of a porous sample under stress is exposing the sample to acoustic waves and analyzing the compressional and shear wave velocities. Methods based on acoustic measurements could be an alternative, but the laboratory setup for acoustic measurements and seismic data analysis is costly. Hence, the acoustic measurements are perceived in the industry as special measurements and they are not routinely used by commercial laboratories.

SUMMARY

This summary is provided to introduce a selection of concepts that are further described below in the Detailed Description. This summary is not intended to identify key or essential features of the claimed subject matter, nor is it to be used as an aid in limiting the scope of the claimed subject matter.

Aspects of the disclosure relate to a system. The system includes a gas tank. A reference volume is fluidly coupled to the gas tank. A coreholder fluidly is coupled to the reference volume. A sample is disposed in the coreholder. A fluid pump is fluidly coupled to the coreholder. A first pressure transducer is fluidly coupled between the fluid pump and the coreholder. The first pressure transducer measures a confining pressure. A second pressure transducer is fluidly coupled to the coreholder. The second pressure transducer measures upstream pressure within the coreholder.

Aspects of the disclosure relate to a method. The method includes disposing a sample in a coreholder. A confining pressure is applied to the coreholder. A gas is admitted from a tank to a reference volume. The gas is allowed to reach equilibrium. The gas is admitted to the coreholder. The gas is allowed to permeate the sample. The confining pressure and the upstream pressure are recorded.

Aspects of the disclosure relate to a method. The method includes disposing a sample in a coreholder. The sample is subjected to a first confining pressure. A gas is allowed to permeate the sample at the first confining pressure. First expansion properties of the gas at the first confinement pressure are determined. The sample is subjected to a second confinement pressure. The gas is allowed to permeate the sample at the second confinement pressure. Second expansion properties of the gas at the second confinement pressure are determined. An effective stress coefficient and a pore compressibility of the sample is determined from the first expansion properties and the second expansion properties.

BRIEF DESCRIPTION OF THE DRAWINGS

A more complete understanding of the subject matter of the present disclosure may be obtained by reference to the following Detailed Description when taken in conjunction with the accompanying Drawings wherein:

FIG. 3A is a plot of estimated pore volume as a function of stress for sandstone according to aspects of the disclosure;

FIG. 3B is plot of estimated pore volume as a function of stress for shale according to aspects of the disclosure;

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

Figure 1:
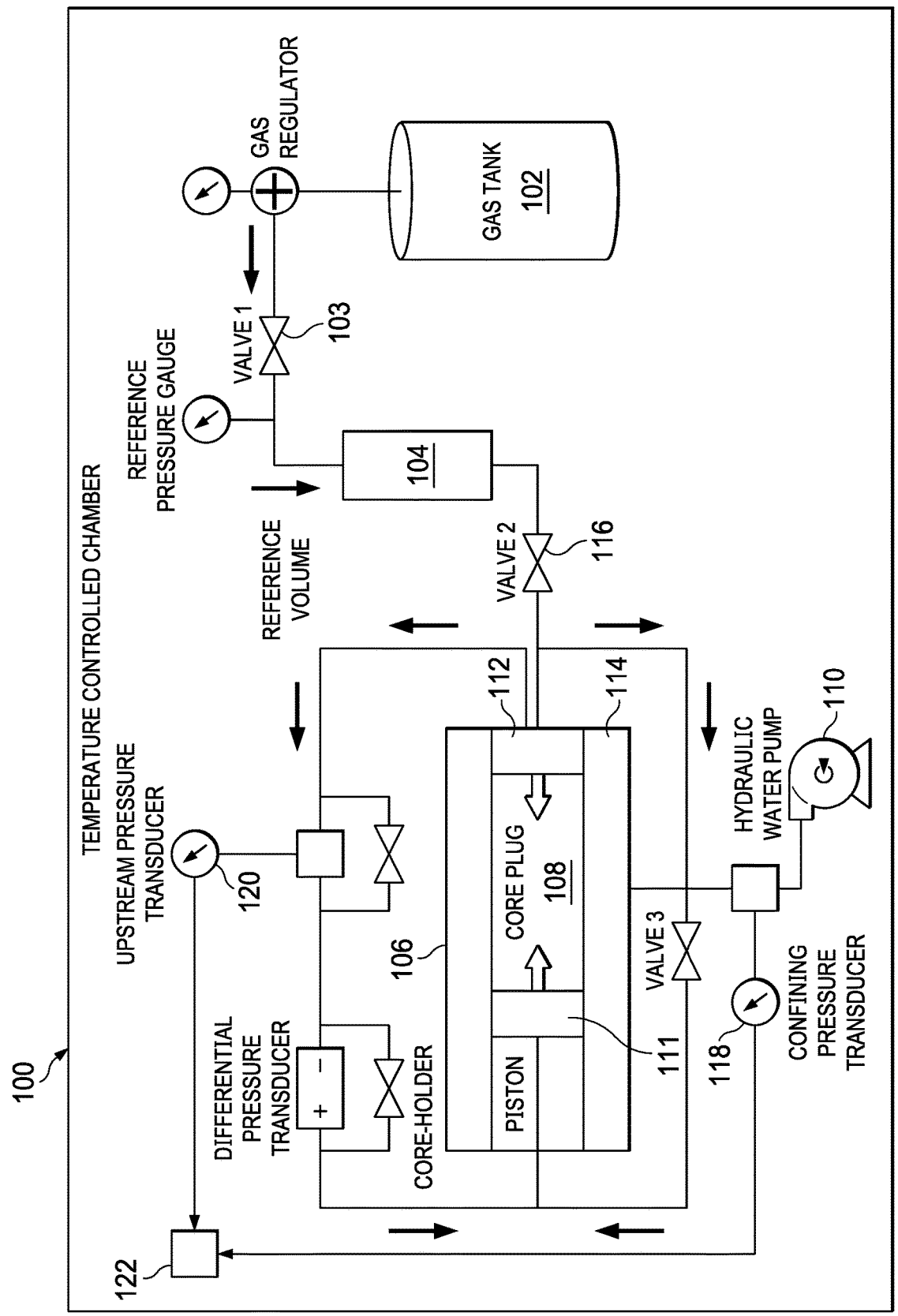
FIG. 1 is a schematic diagram of an apparatus according to aspects of the disclosure.

FIG. 1 is a schematic diagram of an apparatus 100. The setup includes a gas tank 102, an upstream reference volume 104. A first valve 103 is disposed between and fluidly coupled to the reference volume 104 and the gas tank 102. The reference volume 104 is fluidly connected to a coreholder 106, which contains a porous sample 108. A pump 110 is used to confine the sample 108 radially to a confining pressure $P_c$. A rubber sleeve 112 is disposed inside the coreholder 106 and separates the water 114 from the sample 108. The coreholder 106 includes an internal rubber sleeve 112 separating the sample 108 from the walls of the coreholder. A piston 111 is disposed in the coreholder 106 and is used to position the sample 108 within the coreholder 106. In various embodiments, the piston 111 may be hydraulically actuated, for example, using fluid supplied by the pump 110. In other embodiments, the piston 111 may be, for example, pneumatically or mechanically actuated. Water is injected into an annular gap formed between the rubber sleeve 112 and wall by means of the hydraulic pump 110. In various embodiments, injection of the water 114 permits a confinement pressure to be applied on the sample 108. In various embodiments, the coreholder 106 is capable of withstanding pressures up to 10,000 psi and confining pressure is applied up to 5000 psi. A confinement pressure transducer 118 is operatively coupled between the pump 110 and the coreholder 106 and measures confinement pressure. An upstream pressure transducer 120 is operatively coupled to the coreholder 106 and measures upstream pressure. In various embodiments, both the confinement pressure as well as the internal fluid pressures are recorded. In various embodiments, the pressures can be recorded by a data acquisition unit 122 for a desired time interval. Surrounding lines, fittings and valves are considered part of the dead volume $V_d$, which also needs to be considered during the analysis for accuracy. In various embodiments, the components of the apparatus 100 such as, for example, the first valve 103, the second valve 116, tubing, and fittings are rated to 5,000-10,000 psig. These components hold an additional but small volume for the gas storage. Estimation of this dead volume ($V_d$) facilitates accuracy in the measurements especially for low porosity rocks and at high pore pressure. The pore pressure $P_s$ of the sample 108 in the coreholder 106 is adjusted by transferring a portion of the gas from the reference volume 104 using a second valve 116.

The pore volume of a cylindrical sample is measured using a Hassler-type coreholder system, where axial and radial stresses can be applied to the sample as desired. Initially the reference volume 104 is filled with gas at a known pressure and volume and is connected to the coreholder 106 with the sample 108 under constant confining pressure. During the measurement, gas in the reference volume 104 is allowed to expand into the sample pore volume using the second valve 116. Pressure data is collected during the gas expansion using the confinement pressure transducer 118 and the upstream pressure transducer 120 and the fluid pressure equilibration. Applied confining pressure and temperature are maintained constant during the measurement but, in various embodiments, the effective stress the sample 108 experiences could change. Effective stress is the external stress that, if applied in isolation, would produce the same effect as the combination of the applied confining pressure and the pore (or fluid) pressure. The effective stress the sample experiences during the measurement is equal to [applied confining pressure]−[effective stress coefficient]×[applied pore pressure].

Initially, the first valve 103 and the second valve 116 are closed and the coreholder 106 has the sample 108 under stress at some desired $P_c$ and $P_s$. During operation, to complete a stage of gas expansion, first gas from the gas tank 102 is admitted to the reference volume 104, using the first valve 103 at a target pressure $P_r$. Then, the first valve 103 is closed and gas is allowed to reach equilibrium over a time period of, for example, approximately 30 minutes. In various embodiments, helium gas is used as the measurement fluid because helium is an inert gas with a relatively small kinetic diameter of molecules sufficient to reach into smallest pores of the samples 108. Helium exhibits high diffusivity, which is also an advantage. In various embodiments, the helium is contained in the gas tank 102 that supplies up to 1,800 psig. Hence, in various embodiments, a compressing system including a syringe pump and an accumulator may be added for measurements at higher pressures. Next, the second valve 116 is opened and gas is allowed to expand into the coreholder 106 and permeate the sample 108. Depending on the permeability of the sample 108, gas expansion into the sample 108 may, in various embodiments, take, for example, between approximately six and approximately twelve hours. Eventually, the apparatus 100 reaches equilibrium, when the gauges recording the pressure values in the reference volume 104 and in the coreholder 106 read the equilibrium pressure Pf. This equilibrium pressure is the target pressure of interest in the gas uptake process. The process is then repeated for the next stage of gas expansion by allowing more gas into the reference volume 104, and then letting the gas permeate the sample 108. The hydraulic water pump 110 keeps the desired confinement pressure around the sample 108. The confinement pressure transducer 118 is operatively coupled between the pump 110 and the coreholder 106 and measures confinement pressure. The upstream pressure transducer 120 is operatively coupled to the coreholder 106 and measures upstream pressure. The confinement pressure transducer 118 and the upstream pressure transducer 120 are electrically coupled to a data acquisition unit 122 and transmit pressure information to the data acquisition unit 122. In various embodiments, several gas uptake stages can be performed for the same sample 108. In some embodiments, at least two consecutive stages are used to solve for the unknowns $C_p$ and n simultaneously.

In various embodiments, the applied pressures can be controlled by the operator; however, the effective stress coefficient is a mechanical property of the sample 108 and is unknown during the fluid storage measurements. Separate tests, such as a triaxial compaction test, can be used to measure the effective stress coefficient. These tests give the coefficient as the ratio of the bulk volume and grain volume moduli. In the case of samples with isotropic mechanical properties, the effective stress coefficient is reduced to the Biot's coefficient. Thus, it is common to refer to the effective stress coefficient as the Biot's coefficient.

In the present disclosure, the measured volumes and pressures of the reference volume 104 and the coreholder 106 in a gas-mass balance that accounts for the pore-volume change due to change in the effective stress are used. The gas-mass balance is then utilized to determine the pore compressibility coefficient and the Biot's coefficient. The pore compressibility coefficient is a property of the sample related to the storage of fluid, whereas the Biot's coefficient is a mechanical property of the sample related to how the sample experiences the applied confining and pore pressures. Two-stage gas expansion at two separate effective stress values is used to predict these two quantities simultaneously.

Figure 2:
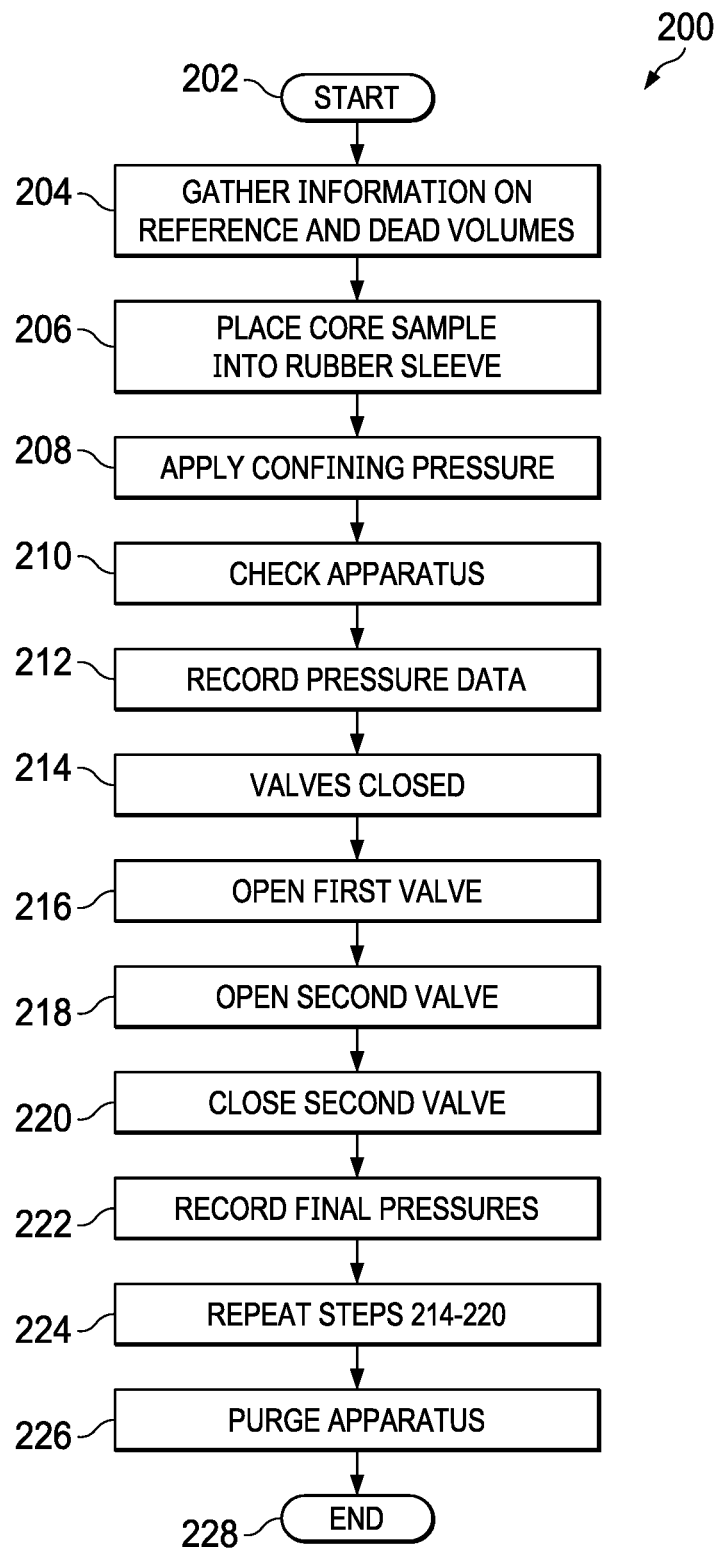
FIG. 2 is a flow diagram illustrating a process for porosity testing according to aspects of the disclosure.

FIG. 2 is a flow diagram illustrating a process 200 for porosity testing. The process 200 begins at step 202. At step 204, information is gathered on the reference and dead volumes ($V_r$ and $V_d$) in the apparatus 100. In various embodiments, the dead volumes may be obtained either by injecting water into the apparatus 100 and keeping track of volumes injected by aid of a hydraulic pump, or using gas expansion and applying Boyle's law to calculate volumes from the pressures measured. At step 206, the sample 108 is placed into the rubber sleeve 112. The end caps are closed, for example, by tightening the screws. A position of the sample 108 is adjusted by pushing the piston 111 within of the coreholder 106, care no gaps are left between the sample 108 and the borders of the coreholder 106. At step 208, a confining pressure is applied to the sample 108 via the hydraulic pump 110. At step 210, the apparatus 100 is checked to verify that pressure gauges match transducer readings and that the interior of the coreholder 106 is under atmospheric pressure. At step 212, pressure data from the transducers is recorded using the data acquisition unit 122. In various embodiments, data may be collected, for example, every second, and filtered/averaged for the analysis, for example, every 60 seconds. At step 214, the apparatus 100 is checked to ensure that the first valve 103 and the second valve 116 are initially closed, and the desired confining pressure is established within the coreholder 106. Then, the first valve 103 that is connected to the gas tank 102 is opened to release gas to the dead volume upstream of the first valve 103 using the regulator to desired pressure.

Still referring to FIG. 2, at step 216, the first valve 103 is opened to charge the reference volume 104 to the desired pressure. Once the target pressure is reached, the first valve 103 is closed and the reference volume 104 is allowed reach equilibrium for a period of time such as, for example, approximately 60 minutes. At step 218, the second valve 116 is opened to admit gas into the coreholder 106 and reach the desired pore pressure. In various embodiments, a small differential pressure (20-30 psi) is maintained during the uptake. The apparatus 100 is allowed to reach equilibrium over a period of time of, for example, approximately, 6-12 hours, depending on the type and properties of the sample 108. At step 220, the second valve 116 is closed to isolate the reference volume 104 from the coreholder 106. The apparatus 100 is allowed to reach equilibrium. At step 222, the final pressure values are read and the corresponding ratio $$a = \frac{p_c}{p_f}$$

is recorded. At step 224, steps 214-220 are repeated until the desired number of pressure stages is reached. In various embodiments, at least two consecutive pressure stages are performed in order to solve for the parameters n and $C_p$ simultaneously. At step 226, the apparatus 100 is purged using the second valve 116. The process 200 ends at step 228.

The analysis, as disclosed herein, utilizes the collected gas expansion data, and solves for the two unknowns, namely the effective stress coefficient, n, and pore compressibility $C_p$, using two coupled algebraic equations, where each equation is written using data from a particular gas-expansion stage. Table 1, shown below, summarizes two separate stages of data.

TABLE 1

| Stages | Pc (psia) | Pr (psia) | Pd (psia) | Ps (psia) | Pf (psia) | Zr | Zd | Zs | Zf |
|---|---|---|---|---|---|---|---|---|---|
| 1 | 600 | 165.7 | 14.6 | 14.6 | 122.5 | 1.0075 | 1.0006 | 1.0006 | 1.0055 |
| 2 | 900 | 197.5 | 14.6 | 14.6 | 146.3 | 1.0090 | 1.0006 | 1.0006 | 1.0066 |

As shown in Table 1 above, $Z_s$, $Z_r$, $Z_d$ are the gas compressibility factors of helium showing the deviation from the ideal gas behavior. In various embodiments, validation of the measurements and the analysis method can be done by taking the two stages at conditions close to zero stress (for example, 0-50 psi pore pressure; 0-100 confinement pressure) and predict the reference pore volume at zero stress, Vp0. In various embodiments, the latter can be measured separately using the standard helium porosimeter.

Using the first two stages, the algebraic equations can be written as follows.

For the first stage:

$$C_p = \frac{\frac{A_1}{V_{p0}} + B_1}{n \times C_1} \quad \text{(Eq. 1)}$$

where reference volume $V_{p0}$ at reference pressure $P_{c0} = 14.7$ psia is known and $A_1$, $B_1$, $C_1$ can be calculated using the first stage of laboratory data:

$$A_1 = V_r\left(\frac{P_{rf}}{Z_{rf}} - \frac{P_{ri}}{Z_{ri}}\right) - V_d\left(\frac{P_{df}}{Z_{df}} - \frac{P_{di}}{Z_{di}}\right) \quad \text{(Eq. 1A)}$$

$$B_1 = \frac{P_{sf}}{Z_{sf}} - \frac{P_{si}}{Z_{si}} \quad \text{(Eq. 1B)}$$

$$C_1 = \frac{P_{si}}{Z_{si}}\left(\frac{P_{cavgi}}{\sigma_{avgi}}\right)(p_{si} - p_0) - \frac{P_{sf}}{Z_{sf}}\left(\frac{P_{cavgf}}{\sigma_{avgf}}\right)(p_{sf} - p_0) \quad \text{(Eq. 1C)}$$

Here, the subscripts i and f correspond to the initial and final conditions during the gas expansion.

Subscripts r, d and s, refer to reference, dead and sample-pore volumes.

For the second stage:

$$C_p = \frac{\frac{A_2}{V_{p0}} + B_2}{n \times C_2} \quad \text{(Eq. 2)}$$

Here, $A_2$, $B_2$, $C_2$ values can be calculated using equations (1A), (1B), and (1C) with the data of the second stage of gas expansion. In the above equations the following quantities are also introduced:

$$P_{c,avg,i} = 2 \times P_{c0} \times P_{ci}$$

$$P_{c,avg,f} = 2 \times P_{c0} \times P_{cf}$$

$$\sigma_{avg,i} = 2 \times P_{c0} \times P_{ci-n} \times P_{ci} \times P_{s0-n} \times P_{c0} \times P_{si}$$

$$\sigma_{avg,f} = 2 \times P_{c0} \times P_{cf-n} \times P_{cf} \times P_{s0-n} \times P_{c0} \times P_{sf}$$

Assuming pore compressibility stays constant between two consecutive stages, which is a reasonable assumption if the applied pressures of the second stage are not changed drastically compared to the first stage values, then Equation (1) and Equation (2) can be combined as follows:

$$\frac{\frac{A_1}{V_{p0}} + B_1}{n \times C_1} - \frac{\frac{A_2}{V_{p0}} + B_2}{n \times C_2} = 0 \quad \text{(Eq. 3)}$$

Equation (3) has only one unknown, which is the coefficient of effective stress, n. The value of n can be obtained using a numerical method where the initial value of 1.0 is assigned. Once n is known, the coefficient of isothermal pore compressibility, $C_p$, can be determined from any of the equations (1) and (2). For the analysis in the laboratory, laboratory data is utilized as input and estimates the two coefficients. A typical output appears as shown in Table 2:

TABLE 2

| Sample #: Shale 4 | | | | |
|---|---|---|---|---|
| σi(psia), | σf (psia) | n(dimensionless), | Cp (1/psi), | Vp (cc) |
| 387 | 646 | 1.738 | 1.1287E−05 | 1.0574 |

The results can be reported in terms of the average effective stress which could be taken as equal to $$\frac{\sigma_i + \sigma_f}{2}.$$

FIGS. 2A-2B show example measurements of two rock samples using the systems and methods as disclosed herein.

Experimental Results

FIG. 3A is a plot of estimated pore volume as a function of stress for sandstone. FIG. 3B is plot of estimated pore volume as a function of stress for shale. Referring to FIGS. 3A-3B, the sandstone sample presents small variations in pore volume due to stress change, while the shale sample shows only a slight change due to such variations in stress. This indicates, that the pore volume is insensitive to stress changes throughout measurements for the case of sandstone and has some sensitivity for the case of shale.

Figure 4B:
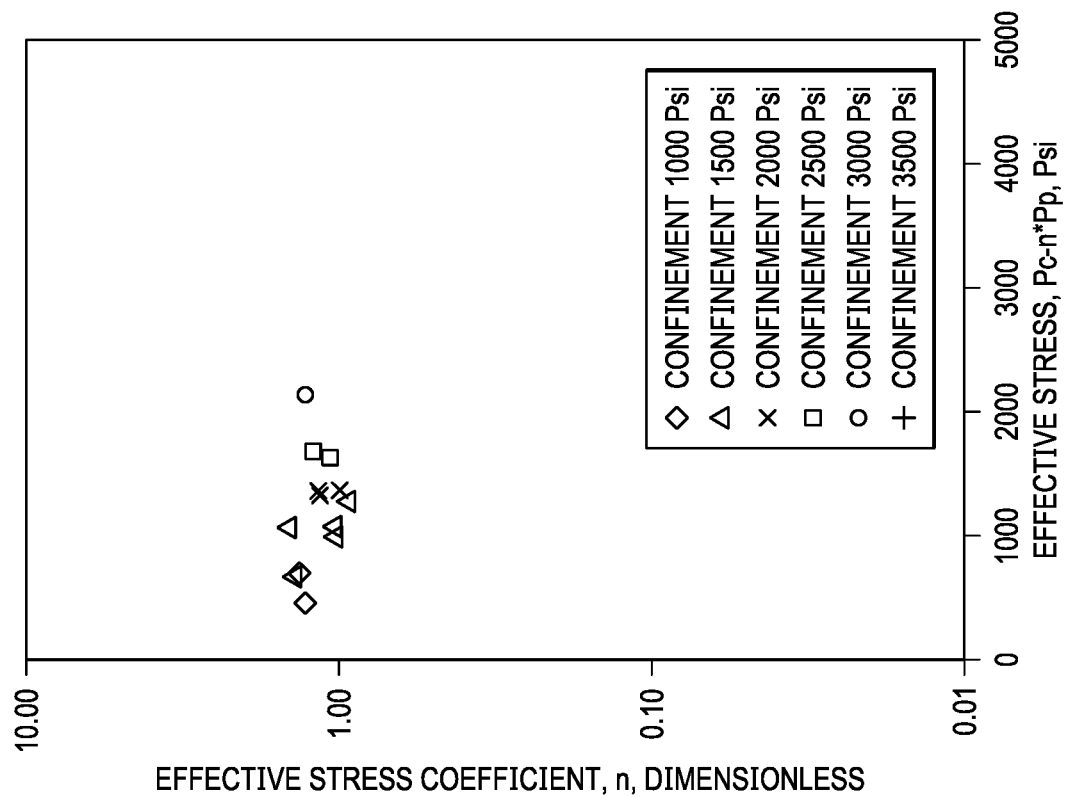
FIG. 4B is a plot of the effective stress coefficient as a function of effective stress for sandstone according to aspects of the disclosure.
Figure 4A:
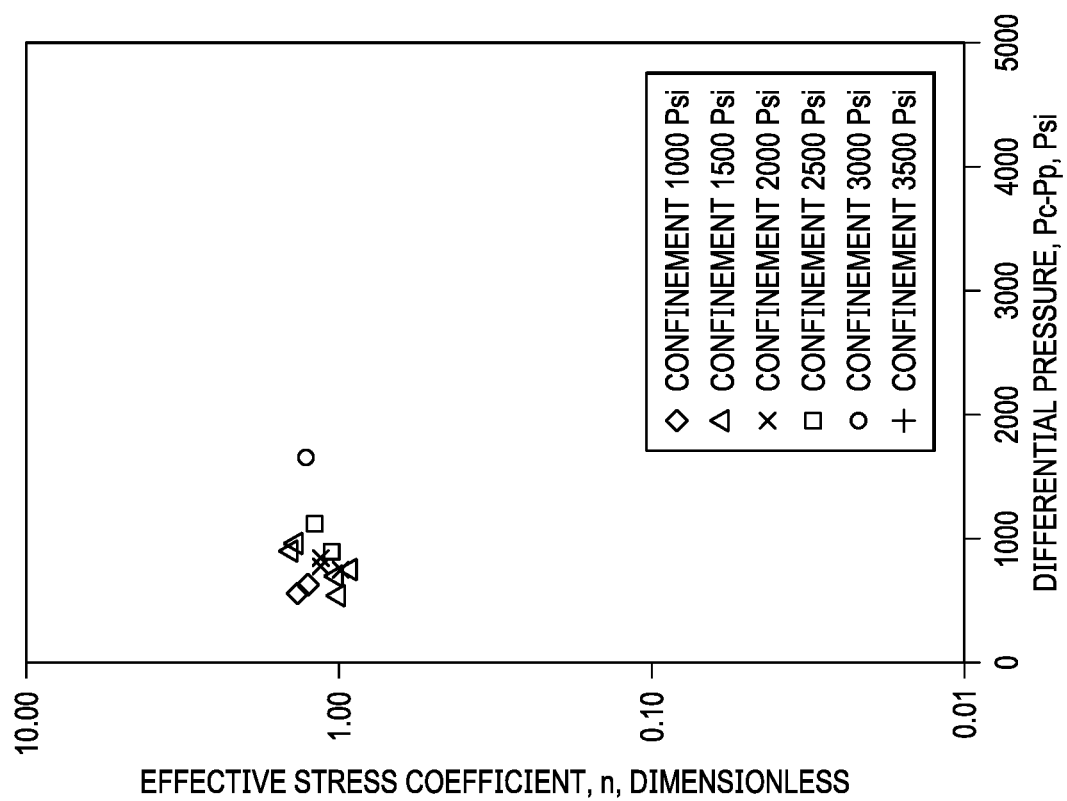
FIG. 4A is a plot of the effective stress coefficient as a function of differential pressure for sandstone according to aspects of the disclosure.
Figure 4D:
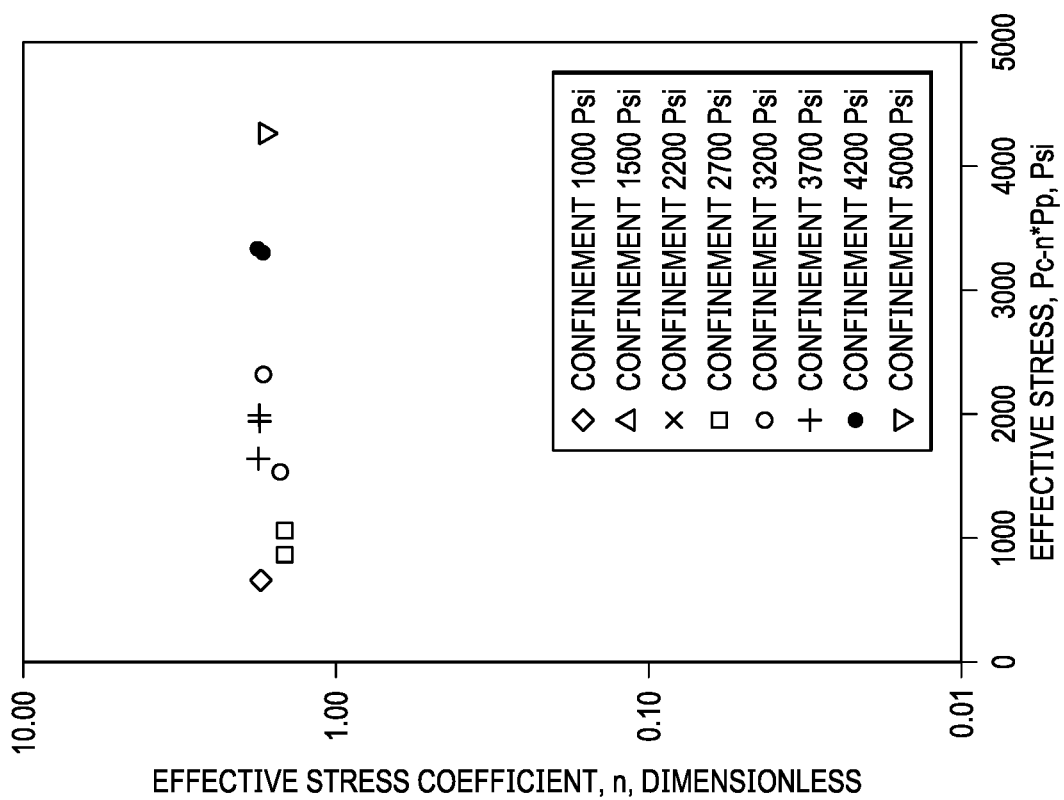
FIG. 4D is a plot of the effective stress coefficient for shale as a function of effective stress according to aspects of the disclosure.
Figure 4C:
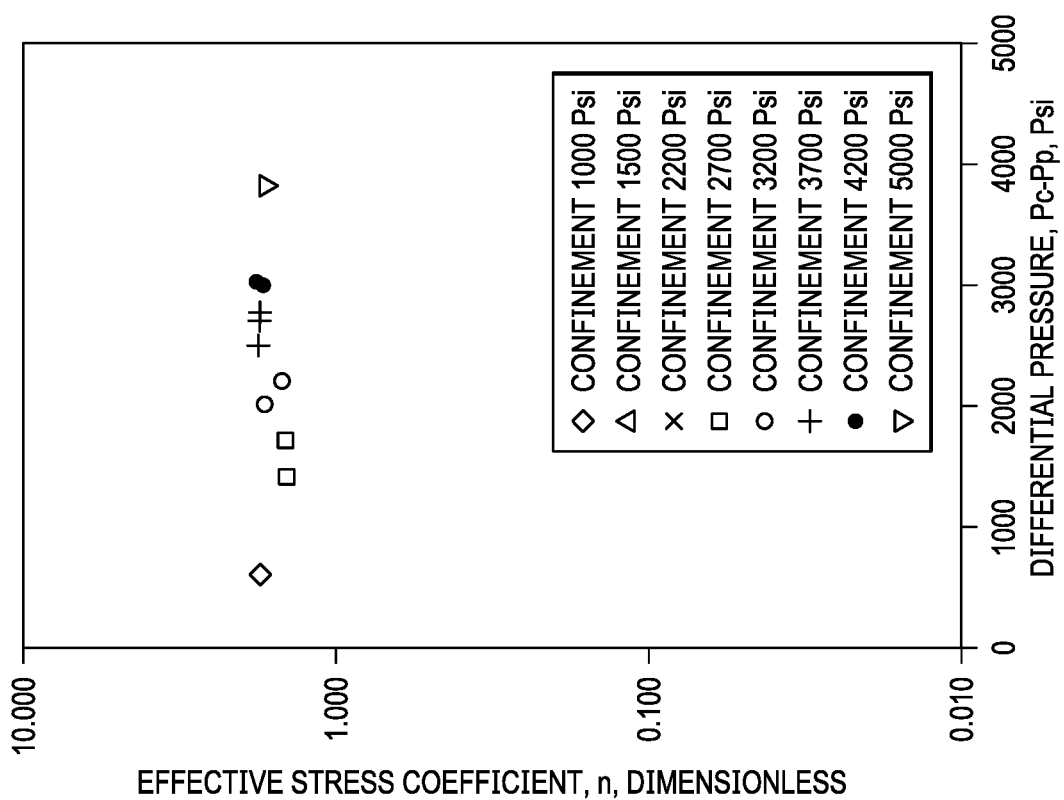
FIG. 4C is a plot of the effective stress coefficient for shale as a function of differential pressure according to aspects of the disclosure.

FIG. 4A is a plot of the effective stress coefficient as a function of differential pressure for sandstone. FIG. 4B is a plot of the effective stress coefficient as a function of effective stress for sandstone. FIG. 4C is a plot of the effective stress coefficient for shale as a function of differential pressure. FIG. 4D is a plot of the effective stress coefficient for shale as a function of effective stress. Referring to FIGS. 4A-4D collectively, the effective stress uses the value of the coefficient at measured data point. Clearly, using the differential pressure as a measure cause the sandstone results to somewhat clustered and without any trend; instead, when the data using the effective stress is displayed as in, for example, FIGS. 4B and 4D, the results are uniformly distributed. In the case of sandstone sample, it was observed that the coefficient with values below approximately 1.5. In the case of shale, the coefficient of effective stress is slightly larger with values between approximately 1.4 and approximately 1.75. A relatively high confining pressure of approximately 5,000 psi was applied to the shale, when the coefficient of effective stress is close to approximately 1.7, so the effective stress did not change greatly. The average value of the coefficient for sandstone is approximately 1.2 while the average value for shale is approximately 1.7.

Effective stress coefficient is a property that weighs the contribution of pore pressure to effective stress. It can be observed from FIGS. 4A-4D how plotting the data considering confinement pressure as third variable, produces several trends. These trends indicate that confinement pressure has a dominant effect on the plug; for instance, in FIG. 4A, having a constant coefficient n at low (approximately 1000-approximately 2000 psi) and high (3500 psi) confinement pressures is producing separate trends meaning the plug is responding mechanically in a different way. The higher the confinement pressure, the higher the effective stress coefficient. FIGS. 4C-4D also show separate trends for the coefficient when confinement pressure is considered as third variable, and the coefficient stays nearly constant when plotted as function of the effective stress.

Figure 5A:
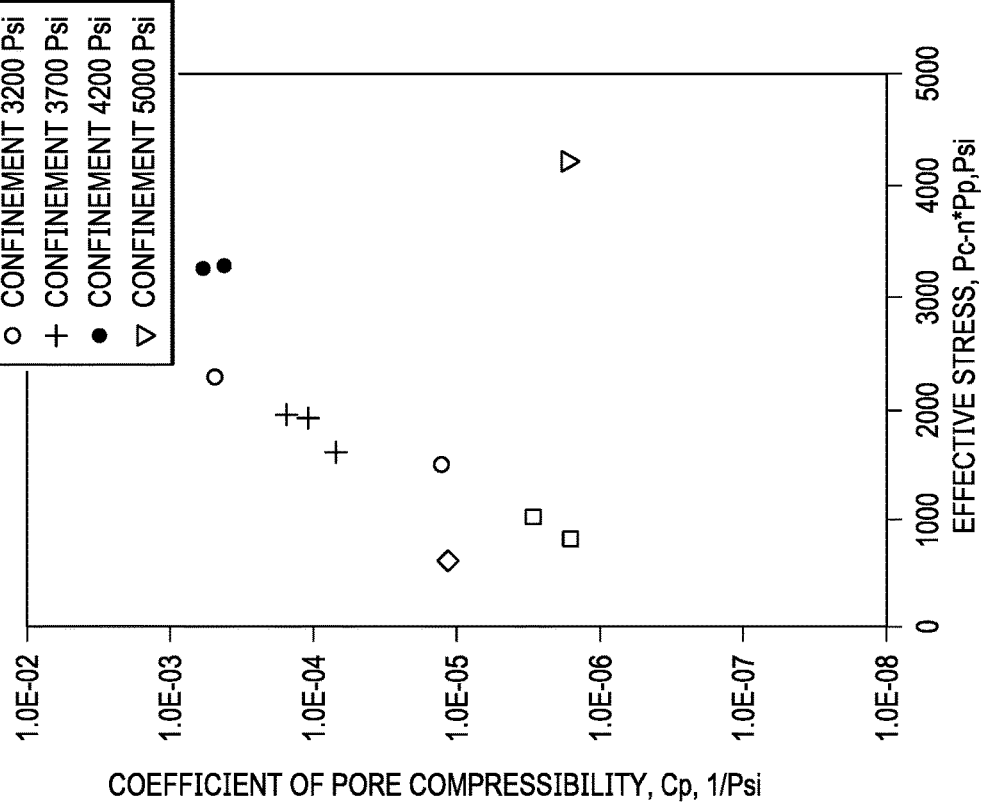
FIG. 5A is a plot of estimated pore compressibility for sandstone as a function of effective stress according to aspects of the disclosure.
Figure 5B:
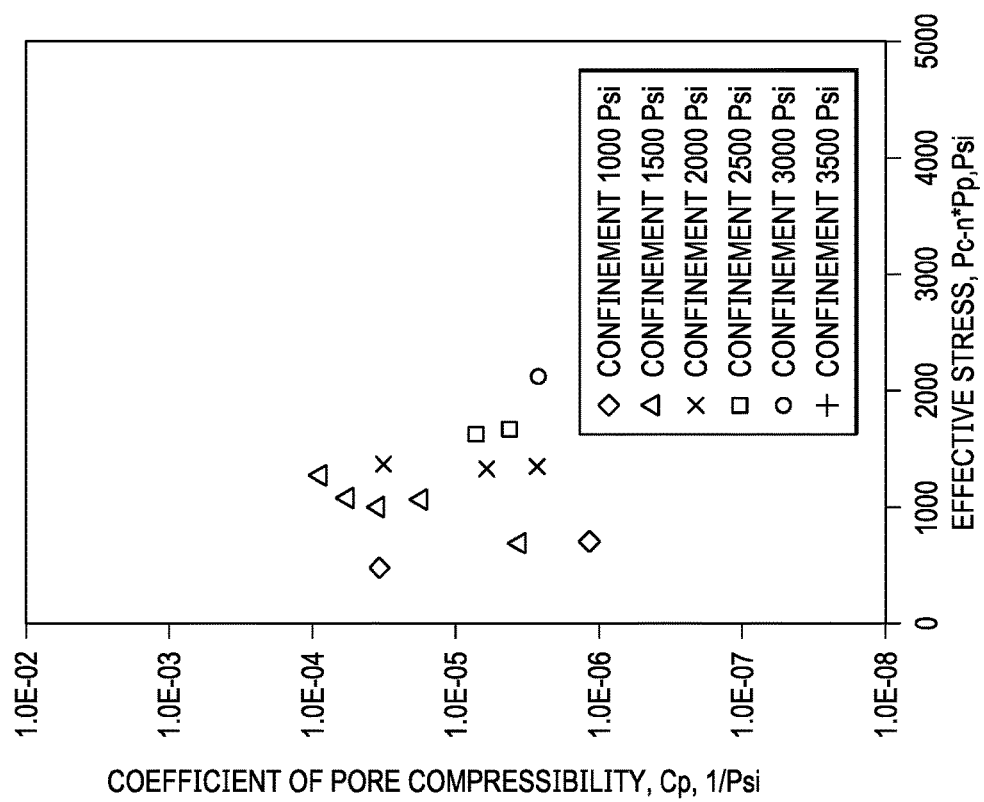
FIG. 5B is a plot of estimated pore compressibility for shale as a function of effective stress according to aspects of the disclosure.

FIG. 5A is a plot of estimated pore compressibility for sandstone as a function of effective stress. FIG. 5B is a plot of estimated pore compressibility for shale as a function of effective stress. FIGS. 5A-5B shows the estimated coefficient of the isothermal pore compressibility, Cp. The average pore compressibility is approximately $2.0 \times 10^{-5}$ 1/psi for sandstone and approximately $2.0 \times 10^4$ for the shale sample, which oscillates more with the applied pressure. The higher values for the coefficient are related to higher pore pressure applied as the uptake gas process progresses. As before, the higher the confinement pressure applied to the core plug, the higher the differential pressure and the effective stress. The compressibility values change two orders of magnitude in between approximately $1.0 \times 10^4$ and approximately $1.0 \times 10^{-6}$ 1/psi.

The systems and methods disclosed herein allow for fast, easy and accurate estimation of the fluid storage capacity of the rock samples (e.g., sandstone, carbonates, mudstones) and other porous materials (e.g., concrete, wood, unglazed ceramic) under effective stress without the need to make separate mechanical tests.

The present disclosure generally relates to systems and methods which takes gas expansion data, the applied confining and pore pressure data, and the geometric measurements of cylindrical porous sample as input, and gives the pore compressibility coefficient (fluid storage property) and the Biot's coefficient (mechanical property) of the sample as output. These coefficients are then used to calculate the storage capacity of the sample as a function of the effective stress. The systems and methods disclosed herein can be used in commercial laboratories as is, or a new user interface can be developed as stand-alone software or as part of existing software. In some embodiments, the results can be reported as tabulated data and as a graph showing the storability as a function of the effective stress.

Gas expansion is commonly used in the oil and gas industry to measure the fluid storage in rock samples and their transport. However, these measurements seldom consider the effects of the applied stress. If they had considered, the results were reported as a function of the applied pressure difference, namely [applied confining pressure]-[applied pore pressure], not the effective stress. The data analysis systems and methods presented herein allow commercial laboratories to use existing gas expansion setups to make the fluid storage measurements under effective stress.

The systems and methods disclosed herein are of interest because the emerging petroleum resources in North America and in the world are increasingly located deeper in the earth under larger overburden stress. These resources have low porosity, with values typically much less than 10%. Low porosity rocks can have measurement error and an unknown effective stress during the measurement can bring in large uncertainties into the analysis. Hence, accurate fluid storage capacity measurements are useful for the economical evaluation of these resources.

The systems and methods disclosed herein can be channeled to the geological and geotechnical laboratories with interest in measuring properties of various rocks, soil and permafrost under stress. The systems and methods disclosed herein can also be used in the structural laboratories with interest in measuring properties of the construction materials such as concrete, wood products and recycled materials. Finally, systems and methods disclosed herein can be used in the materials laboratories with interest in artificial porous materials.

Additional examples of laboratory methods for estimation of storage capacity of rock samples under effective stress according to aspects of the present disclosure can be found in Appendix A, attached herewith.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A system for estimating porosity of a rock sample, the system comprising:
   a gas tank;
   a reference volume fluidly coupled to the gas tank;
   a coreholder fluidly coupled to the reference volume and configured to receive the rock sample;
   a fluid pump fluidly coupled to the coreholder to provide confining pressure on the rock sample;
   a first pressure transducer fluidly coupled between the fluid pump and the coreholder, the first pressure transducer measuring the confining pressure on the rock sample; and
   a second pressure transducer fluidly coupled to the coreholder, the second pressure transducer measuring an upstream pressure that is a pore pressure within the rock sample after a pressurized gas from the reference volume enters the coreholder; and
   a data acquisition unit electrically coupled to the first pressure transducer and the second pressure transducer, wherein the data acquisition unit is configured to:
      collect gas expansion data based on the reference volume, the measured confining pressure, and the measured upstream pressure,
      calculate an effective stress coefficient and a pore compressibility coefficient of the sample based on the gas expansion data of at least two consecutive pressure stages, the effective stress coefficient being related to the confining pressure on the rock sample and the pore compressibility coefficient being related to porosity of the sample, and
      estimate porosity of the sample with respect to the confining pressure on the rock sample.

2. The system of claim 1, comprising a piston disposed in the coreholder, the piston positioning the sample.

3. The system of claim 1, comprising a sleeve disposed within the coreholder, the sleeve containing the sample and creating an annular space between the sleeve and a wall of the coreholder.

4. The system of claim 3, wherein the fluid pump injects fluid into the annular space.

5. The system of claim 4, wherein the fluid is water.

6. The system of claim 1, comprising:
   a first valve disposed between the gas tank and the reference volume; and
   a second volume disposed between the reference volume and the coreholder.

7. A method for estimating porosity of a sample, the method comprising:
   disposing a sample in a coreholder;
   applying a confining pressure on the sample in the coreholder;
   admitting a gas from a tank to a reference volume;
   allowing the gas to reach equilibrium;
   admitting the gas from the reference volume to the coreholder;
   allowing the gas to permeate the sample in the core holder to achieve a target pore pressure within the sample; and
   recording the confining pressure on the sample and an upstream pressure that is the target pressure within the sample;
   collecting gas expansion data based on the reference volume, the confining pressure, and the upstream pressure;
   calculating an effective stress coefficient and a pore compressibility coefficient of the sample based on the gas expansion data of at least two consecutive pressure stages, the effective stress coefficient being related to the confining pressure on the sample and the pore compressibility coefficient being related to porosity of the sample; and estimating porosity of the sample with respect to the confining pressure on the sample.

8. The method of claim 7, wherein the gas is helium.

9. The method of claim 7, wherein:
the admitting the gas from the tank to the reference volume comprises opening a first valve; and
the admitting the gas to the coreholder comprises closing the first valve and opening a second valve.

10. The method of claim 7, wherein the allowing the gas to reach equilibrium occurs over a time period of approximately 30 minutes.

11. The method of claim 7, wherein the allowing the gas to permeate the sample occurs over a time period of approximately six hours to approximately twelve hours.

12. The method of claim 7, wherein the applying the confining pressure comprises injecting water into the coreholder with a fluid pump.

13. The method of claim 12, wherein the water is injected into an annulus formed between a sleeve covering the sample in the coreholder and a wall of the coreholder.

14. A method for estimating porosity of a sample, the method comprising:
disposing a sample in a coreholder;
subjecting the sample to a first confining pressure;
allowing a gas at a first target gas pressure to permeate the sample at the first confining pressure;
determining first expansion properties of the gas at the first target gas pressure and the first confining pressure;
subjecting the sample to a second confining pressure;
allowing the gas at a second target gas pressure to permeate the sample at the second confining pressure;
determining second expansion properties of the gas at the second target gas pressure and the second confining pressure; and
calculating an effective stress coefficient and a pore compressibility coefficient of the sample from the first expansion properties and the second expansion properties, the effective stress coefficient being related to the confining pressure on the sample and the pore compressibility coefficient being related to porosity of the sample; and
estimating porosity of the sample with respect to the confining pressure on the sample.

15. The method of claim 14, wherein the first confinement pressure and the second confinement pressure are applied with a fluid pump.

16. The method of claim 15, wherein the fluid pump injects water into the coreholder.

17. The method of claim 15, wherein the gas is helium.

18. The method of claim 14, wherein the first expansion properties and the second expansion properties include a reference volume compressibility factor, a dead volume compressibility factor, a sample compressibility factor, and a final compressibility factor.

19. The method of claim 18, wherein the first expansion properties and the second expansion properties include a confinement pressure, a target pressure, a dead pressure, a pore pressure, and an equilibrium pressure.

* * * * *